United States Patent [19]

Fischer, deceased et al.

[11] B 4,014,904

[45] Mar. 29, 1977

[54] SUBSTITUTED DIHYDRO BENZOFURANYL ESTERS

[75] Inventors: Adolf Fischer, deceased, late of Mutterstadt, Germany, by Caecilia Emma Fischer, administratrix; Wolfgang Rohr, Mannheim; Christian Reitel, Ziegelhausen, both of Germany

[73] Assignee: BASF Aktiengesellschaft, Ludwigshafen (Rhine), Germany

[22] Filed: Dec. 20, 1974

[21] Appl. No.: 534,680

[44] Published under the second Trial Voluntary Protest Program on April 20, 1976 as document No. B 534,680.

[52] U.S. Cl. .............................. 260/346.2 R; 71/88
[51] Int. Cl.$^2$ ...................................... C07D 307/83
[58] Field of Search ............................ 260/346.2 R

[56] References Cited

UNITED STATES PATENTS 3,689,507  9/1972  Gates et al. ................. 260/346.2 R

*Primary Examiner*—Henry R. Jiles
*Assistant Examiner*—Bernard I. Dentz
*Attorney, Agent, or Firm*—Johnston, Keil, Thompson & Shurtleff

[57] ABSTRACT

New and valuable 4-benzofuranyl esters having a good herbicidal action, herbicides containing these compounds as active ingredients, a process for controlling the growth of unwanted plants with these compounds, and a process for their manufacture.

12 Claims, No Drawings

SUBSTITUTED DIHYDRO BENZOFURANYL ESTERS

The present invention relates to new 4-benzofuranyl esters, the preparation of these compounds, their use as herbicides, and herbicides containing these compounds as active ingredients.

It is known (German Laid-Open Application DOS 1,926,139) to use 2,3-dihydro-3,3-dimethyl-2-ethoxybenzofuran-5-yl methanesulfonate as a herbicide; however, its action is poor.

We have now found that benzofuran-5-yl esters of the formula

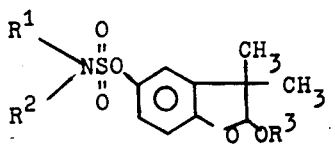

where $R^1$ denotes hydrogen, unsubstituted or halogen (chloro)- or alkoxy (methoxy)-substituted alkyl (methyl, ethyl, propyl, isopropyl, butyl), alkenyl (allyl, methallyl) or alkynyl (propargyl, butynyl) and $R^2$ denotes alkenyl (allyl, methallyl), alkynyl (propargyl, butynyl), a metal atom (alkali metal or alkaline earth metal atom, sodium, potassium, magnesium, lithium), alkylsulfonyl (methylsulfonyl), aminosulfonyl, or acyl of the formula $$-\underset{\underset{O}{\|}}{C}-R^4$$

where $R^4$ denotes unsubstituted or halogen (chloro)-, alkoxy (methoxy)- or alkylthio (thiomethyl)-substituted alkyl, alkenyl or alkynyl, $R^4$ further denotes alkylamino, dialkylamino, or unsubstituted or halogen-substituted alkoxy, and $R^3$ denotes hydrogen, unsubstituted or halogen (chloro)- or alkoxy (methoxy)- substituted alkyl, alkenyl or alkynyl, or acyl of the formula $$-\underset{\underset{O}{\|}}{C}-R^5 ,$$

where $R^5$ denotes unsubstituted or halogen (chloro)-, alkoxy (methoxy)- or alkylthio (thiomethyl)-substituted alkyl, alkenyl or alkynyl, $R^5$ further denotes alkylamino, dialkylamino or unsubstituted or halogen-substituted alkoxy, have a herbicidal action which is superior to that of prior art herbicides, Furthermore, the new compounds have better selectivity in crops such as Gossypium hirsutum, Zea mays and Beta spp. than 2,3-dihydro-3,3-dimethyl-2-ethoxybenzofuran-5-yl methanesulfonate.

The compounds of the invention may be prepared for instance by the following methods:

a. Acylation of benzofuran-5-yl aminosulfonates in accordance with the following equation:

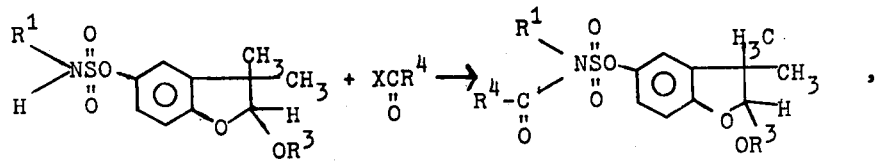

$R^1$, $R^3$ and $R^4$ having the above meanings and X denoting for instance halogen (chloro, bromo) or the radical $$-OCR^4\atop\|\atop O .$$

The benzofuran-5-yl aminosulfonates used as starting materials are known.

b. Acylation of 2-hydroxybenzofuran-5-yl aminosulfonates in accordance with the following equation:

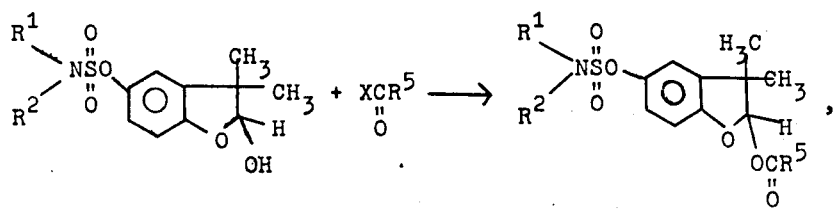

$R^1$, $R^2$ and $R^5$ having the above meanings and X denoting for instance halogen (chloro, bromo) or the radical $$-OCR^5\atop\|\atop O .$$

The benzofuran derivatives used as starting materials may be prepared as follows:

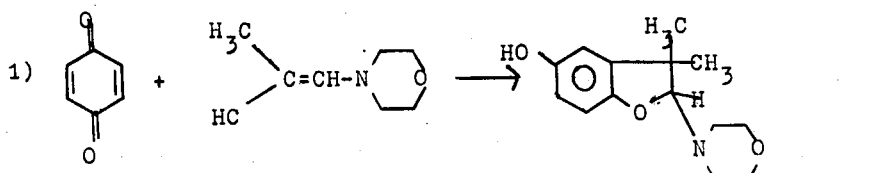

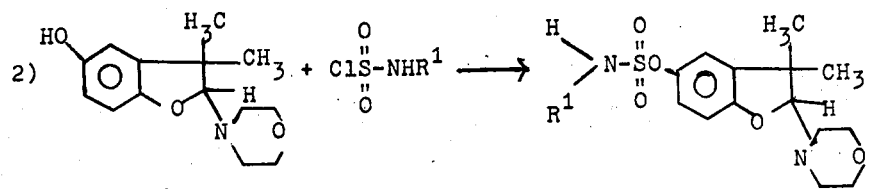

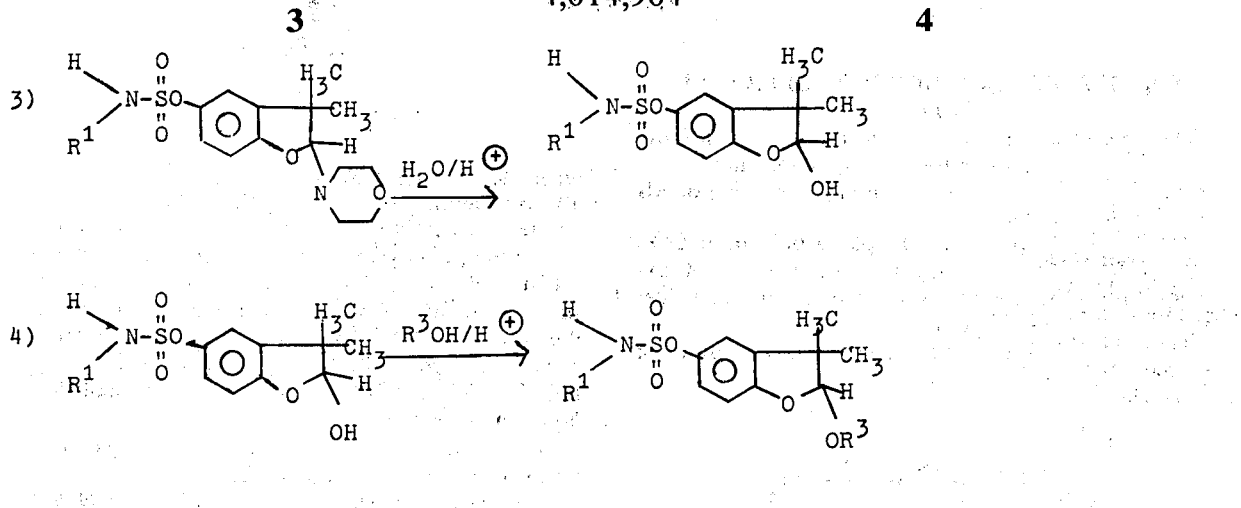

Reaction 1 is known from Dutch Published Application 6,512,311; J. Prakt. Chem., 4th series, 32, 144, 1966; and U.S. 3,184,457.

Reactions 2, 3 and 4 are illustrated by the following experiments.

Experiment A 2,3-dihydro-3,3-dimethyl-2-morpholinobenzofuran-5-yl methylaminosulfonate At 0° to 5°C and while stirring, 36 parts (by weight) of methylaminosulfonyl chloride was added to a solution of 48.8 parts of 2,3-dihydro-3,3-dimethyl-2-morpholino-5-hydroxybenzofuran and 27.3 parts of triethylamine in 130 parts of tetrahydrofuran. The reaction mixture was stirred for 1 hour at room temperature and then filtered. The filtrate was concentrated in vacuo and the residue dissolved in 250 parts of methanol. After addition of 100 parts of water and treatment of the solution with activated carbon, crystallization was initiated by cooling. The mush of crystals was suction filtered, washed with 50wt% aqueous methanol and dried in vacuo. The crude product melted at 125° to 128°C. Pure 2,3-dihydro-3,3-dimethyl-2-morpholinobenzofuran-5-yl methylaminosulfonate was obtained by recrystallizing a sample from 80% methanol. Melting point: 129° to 131°C.

Experiment B 2,3-dihydro-3,3-dimethyl-2-hydroxybenzofuran-5-yl methylaminosulfonate At 80°C and while stirring, 68 parts of 2,3-dihydro-3,3-dimethyl-2-morpholinobenzofuran-5-yl methylaminosulfonate was added all at once to a mixture of 133 parts of water and 68 parts of concentrated hydrochloric acid. The resultant mixture was heated rapidly to 90° to 95°C and kept at this temperature for 2 minutes, after which it was immediately cooled by the addition of ice. The solution was extracted with ether, and the ether solution was washed twice with water, dried with magnesium sulfate and concentrated in vacuo.

The viscous residue was dissolved in 100 parts of ether. 60 parts of n-hexane was added, and 2,3-dihydro-3,3-dimethyl-2-hydroxybenzofuran-5-yl methylaminosulfonate was obtained in the form of crystals upon cooling. Melting point: 111° to 112°C.

The compound has the following structural formula:

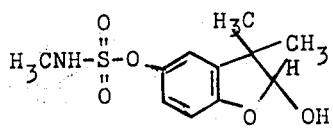

Experiment C 2,3-dihydro-3,3-dimethyl-2-methoxybenzofuran-5-yl methylaminosulfonate 4 drops of concentrated sulfuric acid was added to a solution of 22.5 parts of 2,3-dihydro-3,3-dimethyl-2-hydroxybenzofuran-5-yl methylaminosulfonate in 200 parts of methanol. The mixture was subsequently boiled for 30 minutes under reflux, and then cooled. The mixture was neutralized with triethylamine and concentrated to dryness in vacuo. Treatment of the viscous residue with a mixture of ether and n-hexane gave crystals of 2,3-dihydro-3,3-dimethyl-2-methoxybenzofuran-5-yl methylaminosulfonate; melting point: 89° to 91°C.

The compound has the following structural formula:

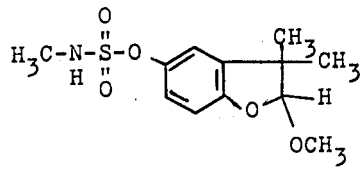

If, in methods a and b, $R^4$ is alkylamino, the acylating agent is an isocyanate - the following equation exemplifies this for methyl isocyanate:

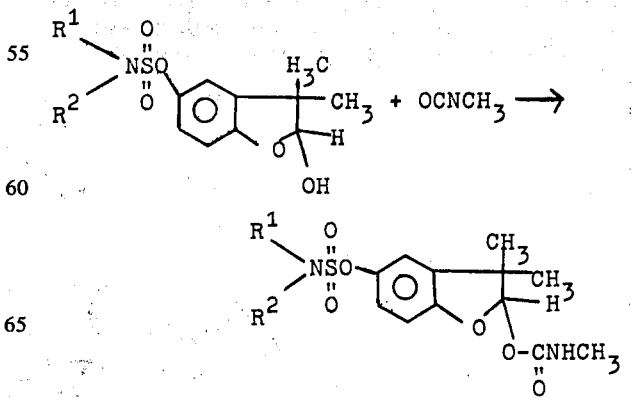

c. Reaction of benzofuran-5-yl aminosulfonates with an alkylsulfonyl halide - the following equation demonstrates this for methylsulfonyl chloride:

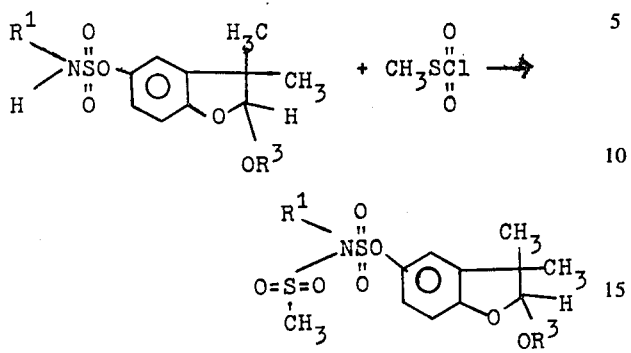

d. Action of metal hydroxides, preferably alkali metal and alkaline earth metal hydroxides, on benzofuran-5-yl aminosulfonates, as is illustrated by the following equation which uses sodium hydroxide by way of example:

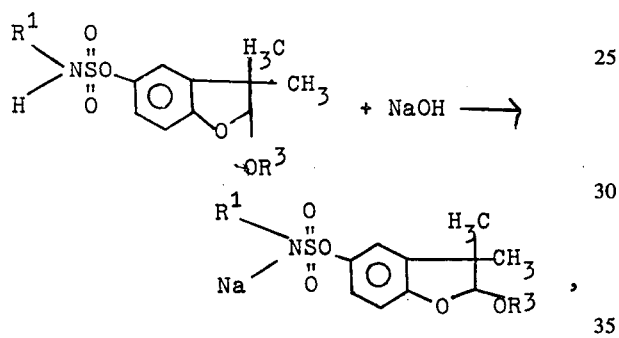

$R^1$ and $R^3$ having the meanings given above.

e. Alkylation of benzofuran-5-yl aminosulfonates with alkenyl or alkynyl halides. There are used as reactants for instance the salts prepared under d), as is demonstrated in the following equation for alkyl bromide:

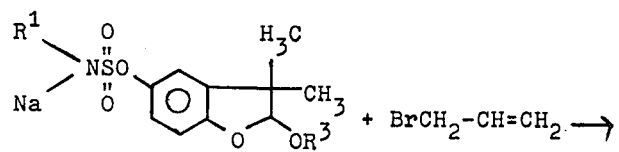

$R^1$ and $R^3$ having the meanings given above.

The following examples illustrate the preparation of the new compounds.

EXAMPLE 1

At 15° to 20°C and while stirring, 9 parts by weight of acetyl chloride was added to a solution of 30.1 parts by weight of 2,3-dihydro-3,3-dimethyl-2-ethoxybenzofuran-5-yl methylaminosulfonate and 12 parts by weight of triethylamine in 90 parts by weight of ether. After 1 hour the reaction mixture was extracted 3 times with water. The ethereal solution was dried with magnesium sulfate, and left, upon concentration in vacuo, an oily residue of the compound 2,3-dihydro-3,3-dimethyl-2-ethoxybenzofuran-5-yl-N-methylcarbonyl methylaminosulfonate which did not crystallize even after standing for a fairly long period of time. $n_D^{25}$: 1.5402

Analysis and infrared and nmr spectra agree well with the following structural formula:

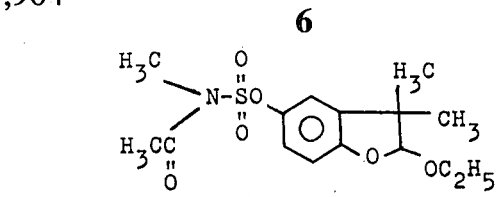

The following compounds were prepared analogously:

2,3-dihydro-3,3-dimethyl-2-methoxybenzofuran-5-yl-N-methylcarbonyl methylaminosulfonate, $n_D^{25}$ : 1.5085

2,3-dihydro-3,3-dimethyl-2-methoxybenzofuran-5-yl-N-methylcarbonyl ethylaminosulfonate 2,3-dihydro-3,3-dimethyl-2-methoxybenzofuran-5-yl-N-ethylcarbonyl methylaminosulfonate 2,3-dihydro-3,3-dimethyl-2-ethoxybenzofuran-5-yl-N-ethylcarbonyl methylaminosulfonate 2,3-dihydro-3,3-dimethyl-2-methoxybenzofuran-5-yl-N-chloromethylcarbonyl methylaminosulfonate, $n_D^{25}$ : 1.5195

2,3-dihydro-3,3-dimethyl-2-ethoxybenzofuran-5-yl-N-chloromethylcarbonyl methylaminosulfonate, $n_D^{25}$ : 1.5140 2,3-dihydro-3,3-dimethyl-2-ethoxybenzofuran-5-yl-N-dichloromethylcarbonyl methylaminosulfonate, $n_D^{25}$ : 1.5165

2,3-dihydro-3,3-dimethyl-2-methoxybenzofuran-5-yl-N-chloromethylcarbonyl ethylaminosulfonate 2,3-dihydro-3,3-dimethyl-2-methoxybenzofuran-5-yl-N-methoxycarbonyl methylaminosulfonate 2,3-dihydro-3,3-dimethyl-2-methoxybenzofuran-5-yl-N-ethoxycarbonyl methylaminosulfonate 2,3-dihydro-3,3-dimethyl-2-methoxybenzofuran-5-yl-N-isopropoxycarbonyl methylaminosulfonate 2,3-dihydro-3,3-dimethyl-2-ethoxybenzofuran-5-yl-N-methoxycarbonyl methylaminosulfonate, $n_D^{25}$ : 1.5000

2,3-dihydro-3,3-dimethyl-2-ethoxybenzofuran-5-yl-N-ethoxycarbonyl methylaminosulfonate, $n_D^{25}$ : 1.4945

2,3-dihydro-3,3-dimethyl-2-ethoxybenzofuran-5-yl-N-isopropoxycarbonyl methylaminosulfonate, $n_D^{25}$ : 1.4880.

EXAMPLE 2

At −8°C to −12°C and while stirring, 10.3 parts by weight of acetyl chloride was added to a solution of 28.7 parts by weight of 2,3-dihydro-3,3-dimethyl-2-hydroxybenzofuran-5-yl dimethylaminosulfonate and 14.1 parts by weight of triethylamine in 110 parts by weight of ether. The mixture was worked up as in Example 1, the compound 2,3-dihydro-3,3-dimethyl-2-methylcarbonyloxybenzofuran-5-yl dimethylaminosulfonate being obtained in the form of crystals; melting point: 67° to 68°C.

The compound has the following structural formula:

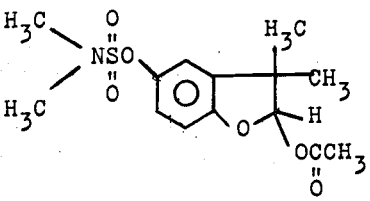

The following compounds were prepared analogously:

2,3-dihydro-3,3-dimethyl-2-ethylcarbonyloxybenzofuran-5-yl dimethylaminosulfonate, m.p. 53° to 54°C 2,3-dihydro-3,3-dimethyl-2-chloromethylcarbonyloxybenzofuran-5-yl dimethylaminosulfonate, m.p. 87° to 88°C 2,3-dihydro-3,3-dimethyl-2-chloromethylcarbonyloxybenzofuran-5-yl diethylaminosulfonate, $n_D^{25}$: 1.5078

2,3-dihydro-3,3-dimethyl-2-dichloromethylcarbonyloxybenzofuran-5-yl dimethylaminosulfonate 2,3-dihydro-3,3-dimethyl-2-dichloromethylcarbonyloxybenzofuran-5-yl diethylaminosulfonate 2,3-dihydro-3,3-dimethyl-2-methoxycarbonyloxybenzofuran-5-yl dimethylaminofulfonate, m.p. 101° to 102°C 2,3-dihydro-3,3-dimethyl-2-ethoxycarbonyloxybenzofuran-5-yl dimethylaminosulfonate, m.p. 84° to 85°C 2,3-dihydro-3,3-dimethyl-2-isopropoxycarbonyloxybenzofuran-5-yl dimethylaminosulfonate 2,3-dihydro-3,3-dimethyl-2-methoxycarbonyloxybenzofuran-5-yl diethylaminosulfonate, m.p. 95° to 96°C 2,3-dihydro-3,3-dimethyl-2-ethoxycarbonyloxybenzofuran-5-yl diethylaminosulfonate 2,3-dihydro-3,3-dimethyl-2-isopropoxycarbonyloxybenzofuran-5-yl diethylaminosulfonate.

EXAMPLE 3

After the addition of 1 part by weight of triethylamine, 6.9 parts by weight of methyl isocyanate was added at room temperature (20°C) to a solution of 28.7 parts by weight of 2,3-dihydro-3,3-dimethyl-2-hydroxybenzofuran-5-yl dimethylaminosulfonate in 90 parts by weight of tetrahydrofuran. The temperature rose slightly, after which the mixture was left for 24 hours. The solvent was then removed in vacuo and the residue recrystallized from ether; melting poing: 101° to 103°C.

The compound, 2,3-dihydro-3,3-dimethyl-2-methylaminocarbonyloxybenzofuran-5-yl dimethylaminosulfonate, has the following structural formula:

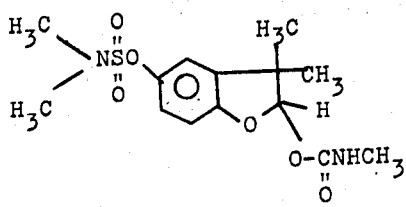

The following compounds were prepared analogously:

2,3-dihydro-3,3-dimethyl-2-ethylaminocarbonyloxybenzofuran-5-yl dimethylaminosulfonate, m.p. 112° to 113°C 2,3-dihydro-3,3-dimethyl-2-propylaminocarbonyloxybenzofuran-5-yl dimethylaminosulfonate 2,3-dihydro-3,3-dimethyl-2-isopropylaminocarbonyloxybenzofuran-5-yl dimethylaminosulfonate, m.p. 107° to 109°C 2,3-dihydro-3,3-dimethyl-2-methylaminocarbonyloxybenzofuran-5-yl diethylaminosulfonate, m.p. 122° to 123°C 2,3-dihydro-3,3-dimethyl-2-ethylaminocarbonyloxybenzofuran-5-yl diethylaminosulfonate, m.p. 124° to 125°C 2,3-dihydro-3,3-dimethyl-2-methylaminocarbonyloxybenzofuran-5-yl methylaminosulfonate 2,3-dihydro-3,3-dimethyl-2-ethylaminocarbonyloxybenzofuran-5-yl methylaminosulfonate 2,3-dihydro-3,3-dimethyl-2-propylaminocarbonyloxybenzofuran-5-yl methylaminosulfonate 2,3-dihydro-3,3-dimethyl-2-isopropylaminocarbonyloxybenzofuran-5-yl methylaminosulfonate.

EXAMPLE 4

At 10°C and while stirring, 56 parts by weight of acetic anhydride was added to a solution of 68 parts by weight of 2,3-dihydro-3,3-dimethyl-2-hydroxybenzofuran-5-yl methylaminosulfonate and 55.5 parts by weight of triethylamine.

After standing overnight, the precipitated reaction product was suction filtered, washed with cold ether and water, and dried in vacuo at 60°C; melting point: 103° to 104°C.

The compound, 2,3-dihydro-3,3-dimethyl-2-methylcarbonyloxybenzofuran-5-yl-N-methylcarbonyl methylaminosulfonate, has the following structural formula:

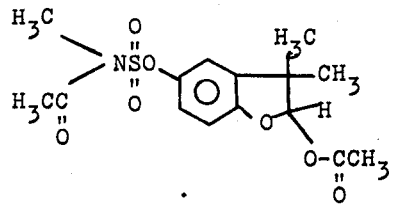

The following compounds were prepared analogously:

2,3-dihydro-3,3-dimethyl-2-chloromethylcarbonyloxybenzofuran-5-yl-N-chloromethylcarbonyl methylaminosulfonate 2,3-dihydro-3,3-dimethyl-2-ethylcarbonyloxybenzofuran-5-yl-N-ethylcarbonyl methylaminosulfonate 2,3-dihydro-3,3-dimethyl-2-methylcarbonyloxybenzofuran-5-yl-N-methylcarbonyl ethylaminosulfonate.

EXAMPLE 5

At −8° to −12°C, a solution of 13.8 parts by weight of methylsulfonyl chloride in 30 parts by weight of dichloromethane was added to a solution of 28.7 parts by weight of 2,3-dihydro-3,3-dimethyl-2-methoxybenzofuran-5-yl methylaminosulfonate and 13.3 parts by weight of triethylamine in 130 parts by weight of dichloromethane. 30 minutes after the reaction was over the mixture was extracted three times with water. The organic phase was dried with magnesium sulfate and freed from solvent in vacuo. The sirupy residue ($n_D^{25}$: 1.5150) did not crystallize even upon standing for a fairly long period of time.

Infrared and nmr spectra and ultimate analysis of the residue agree well with the compound 2,3-dihydro-3,3-dimethyl-2-methoxybenzofuran-5-yl-N-methylsulfonyl methylaminosulfonate having the following structural formula:

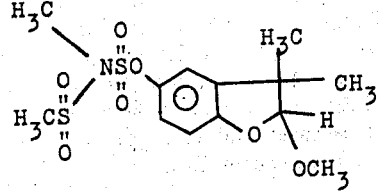

The following compounds were prepared analogously:
2,3-dihydro-3,3-dimethyl-2-ethoxybenzofuran-5-yl-N-methylsulfonyl methylaminosulfonate
2,3-dihydro-3,3-dimethyl-2-methoxybenzofuran-5-yl-N-ethylsulfonyl methylaminosulfonate
2,3-dihydro-3,3-dimethyl-2-ethoxybenzofuran-5-yl ethylsulfonyl methylaminosulfonate.

EXAMPLE 6

After the addition of 0.5 part by weight of triethylamine, 5.15 parts by weight of methyl isocyanate was added to a solution of 20.5 parts by weight of 2,3-dihydro-3,3-dimethyl-2-ethoxybenzofuran-5-yl methylaminosulfonate in 70 parts by weight of tetrahydrofuran. Subsequently, the mixture was left for 48 hours. The solution was then concentrated in vacuo and the residue taken up in ether and treated three times with water. The organic phase was dried with magnesium sulfate, and concentrated in vacuo after having been treated with activated carbon.

$n_D^{25}$ : 1.5085

Infrared and nmr spectra and ultimate analysis of the sirupy residue agree well with the compound 2,3-dihydro-3,3-dimethyl-2-ethoxybenzofuran-5-yl-N-methylaminocarbonyl methylaminosulfonate having the following structural formula:

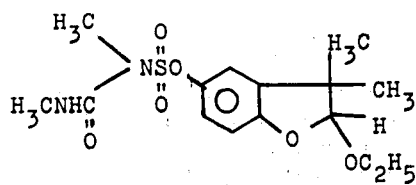

The following compounds were prepared analogously:
2,3-dihydro-3,3-dimethyl-2-methoxybenzofuran-5-yl-N-methylaminocarbonyl methylaminosulfonate
2,3-dihydro-3,3-dimethyl-2-ethoxybenzofuran-5-yl-N-ethylaminocarbonyl methylaminosulfonate
2,3-dihydro-3,3-dimethyl-2-methoxybenzofuran-5-yl-N-ethylaminocarbonyl methylaminosulfonate.

EXAMPLE 7

A solution of 4 parts by weight of sodium hydroxide in 20 parts by weight of water was added to a suspension of 30.1 parts by weight of 2,3-dihydro-3,3-dimethyl-2-ethoxybenzofuran-5-yl methylaminosulfonate in 55 parts by weight of water. From the solution which formed it was possible to obtain the salt by evaporating the water in vacuo.

Infrared and nmr spectra and ultimate analysis of the salt agree well with the compound 2,3-dihydro-3,3-dimethyl-2-ethoxybenzofuran-5-yl methylaminosulfonate, sodium salt, having the following structural formula:

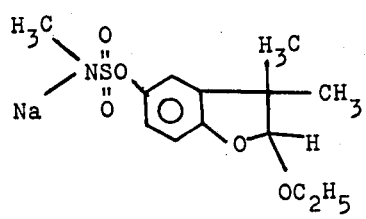

The lithium and potassium salts of the following compounds were prepared analogously:
2,3-dihydro-3,3-dimethyl-2-methoxybenzofuran-5-yl methylaminosulfonate
2,3-dihydro-3,3-dimethyl-2-ethoxybenzofuran-5-yl methylaminosulfonate
2,3-dihydro-3,3-dimethyl-2-methoxybenzofuran-5-yl ethylaminosulfonate
2,3-dihydro-3,3-dimethyl-2-ethoxybenzofuran-5-yl ethylaminosulfonate.

EXAMPLE 8

At 20° to 23°C and while stirring, a solution of 8.5 parts by weight of propargyl bromide in 20 parts by weight of acetone was added to 46 parts by weight of a 50 wt% aqueous solution of the sodium salt of 2,3-dihydro-3,3-dimethyl-2-ethoxybenzofuran-5-yl methylaminosulfonate (prepared as in Example 7). The temperature rose slightly to 29°C. To complete the reaction the mixture was stirred for a further 6 hours at 35°C. Ethyl acetate was then added and extraction was carried out three times with water. The organic phase was dried with magnesium sulfate and subsequently concentrated to dryness in vacuo.

$n_{25}^{25}$ : 1.5085

Infrared and nmr spectra and ultimate analysis of the sirupy residue agree well with the compound 2,3-dihydro-3,3-dimethyl-2-ethoxybenzofuran-5-yl-N-propargyl methylaminosulfonate having the following structural formula:

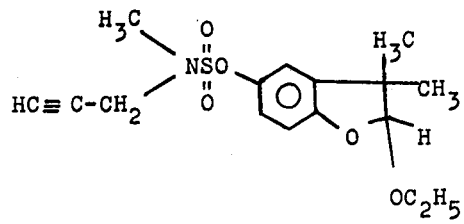

The following compounds were prepared analogously:
2,3-dihydro-3,3-dimethyl-2-ethoxybenzofuran-5-yl-N-allyl methylaminosulfonate, b.p. (0.01 mm) 137° to 146°C, $n_D^{25}$ : 1.5065
2,3-dihydro-3,3-dimethyl-2-ethoxybenzofuran-5-yl propargylaminosulfonate
2,3-dihydro-3,3-dimethyl-2-ethoxybenzofuran-5-yl allylaminosulfonate
2,3-dihydro-3,3-dimethyl-2-methoxybenzofuran-5-yl propargylaminosulfonate
2,3-dihydro-3,3-dimethyl-2-methoxybenzofuran-5-yl allylaminosulfonate
2,3-dihydro-3,3-dimethyl-2-ethoxybenzofuran-5-yl diallylaminosulfonate.

The new active ingredients have a strong herbicidal action and may therefore be used as weedkillers or for controlling the growth of unwanted plants. Whether they are used as total or selective agents depends in essence on the amount of ingredient used per unit area.

By weeds and unwanted plant growth are meant all monocotyledonous and dicotyledonous plants which grow in loci where they are not desired.

The agents according to the invention may therefore be used for controlling for instance Gramineae, such as
  Cynodon spp.
  Digitaria spp.
  Echinochloa spp.
  Setaria spp.
  Panicum spp.
  Alopecurus spp.
  Lolium spp.
  Sorghum spp.
  Agropyron spp.
  Phalaris spp.
  Apera spp.
  etc.;
  Dactylis spp.
  Avena spp.
  Bromus spp.
  Uniola spp.
  Poa spp.
  Leptochloa spp.
  Brachiaria spp.
  Eleusine spp.
  Cenchrus spp.
  Eragrostis spp.
  Phragmites communis
Cyperaceae, such as
  Carex spp.
  Cyperus spp.
  etc.;
  Eleocharis spp.
  Scirpus spp.
dicotyledenous weeds, such as
Malvaceae, e.g.,
  Abutilon theoprasti
  Sida spp.
  etc.;
  Hibiscus spp.
  Malva spp.
Compositae, such as
  Ambrosia spp.
  Lactuca spp.
  Senecio spp.
  Sonchus spp.
  Xanthium spp.
  Iva spp.
  Galinsoga spp.
  Taraxacum spp.
  Chrysanthemum spp.
  Cirsium spp.
  Centaurea spp.
  Tussilago spp.
  Lapsana communis
  Tagetes spp.
  Erigeron spp.
  Anthemis spp.
  Matricaria spp.
  Artemisia spp.
  Bidens spp.
  etc.;
Convolvulaceae, such as
  Convolvulus spp.
  Ipomea spp.
  etc.;
  Cuscuta spp.
  Jaquemontia tamnifolia
Cruciferae, such as
  Barbarea vulgaris
  Brassica spp.
  Capsella spp.
  Sisymbrium spp.
  Thlaspi spp.
  Sinapis arvensis
  etc.;
  Arabidopsis thaliana
  Descurainia spp.
  Draba spp.
  Coronopus didymus
  Lepidium spp.
  Raphanus spp.
Geraniaceae, such as
  Erodium spp.
  etc.;
  Geranium spp.
Portulacaceae, such as
  Portulaca spp.
Primulaceae, such as
  Anagallis arvensis
  etc.
  etc.,
  Lysimachia spp.
Rubiaceae, such as
  Richardia spp.
  Galium spp.
  Diodia spp.
  etc.;
Scrophulariaceae, such as
  Linaria spp.
  Veronica spp.
  Digitalis spp.
  etc.;
Solanaceae, such as
  Physalis spp.
  Solanum spp.
  etc.;
  Nicandra spp.
  Datura spp.
Urticaceae, such as
  Urtica spp.
Violaceae, such as
  Viola spp.
  etc.;
Zygophyllaceae, such as
  Tribulus terrestris
  etc.;
Euphorbiaceae, such as
  Mercurialis annua
  Euphorbia spp.
Umbelliferae, such as
  Daucus carota
  Aethusa cynapium
  Ammi majus
  etc.;
Commelinaceae, such as
  Commelina spp.
  etc.;
Labiatae, such as
  Lamium spp.
  etc.;
  Galeopsis spp.
Leguminosae, such as
  Medicago spp.
  Trifolium spp.
  Vicia spp.
  etc.;
  Sesbania exaltata
  Cassia spp.
  Lathyrus spp.
Plantaginaceae, such as
  Plantago spp.
  etc.;
Polygonaceae, such as
  Polygonum spp.
  Rumex spp.
  Fagopyrum spp.
  etc.;
Aizoaceae, such as
  Mollugo verticillata
  etc.;
Amaranthaceae, such as
  Amaranthus spp.
  etc.;
Boraginaceae, such as
  Amsinckia spp.
  Myostis spp.
  etc.;
  Anchusa spp.
  Lithospermum spp.
Caryophyllaceae, such as
  Stellaria spp.
  Spergula spp.
  Saponaria spp.
  Scleranthus annuus
  Silene spp.
  Cerastium spp.
  Agrostemma githago
  etc.;
Chenopodiaceae, such as
  Chenopodium spp.
  Kochia spp.
  Salsola Kali
  Atriplex spp.
  Monolepsis nuttalliana
  etc.;
Lythraceae, such as
  Cuphea spp.
  etc.;
Oxalidaceae, such as
  Oxalis spp.
Ranunculaceae, such as
  Ranunculus spp.
  Delphinium spp.
  Adonis spp.
  etc.;
Papaveraceae, such as
  Papaver spp.
  etc.;
  Fumaria officinalis
Onagraceae, such as
  Jussiaea spp.
  etc.;
Rosaceae, such as
  Alchemillia spp.
  etc.;
  Potentilla spp.
Potamogetonaceae, such as
  Potamogeton spp.
  etc.;
Najadaceae, such as
  Najas spp.
  etc.;
Equisetaceae
  Equisetum spp.
  etc.;
Marsileaceae, such as
  Marsilea quadrifolia
  etc.;
Polypodiaceae,
  Pteridium quilinum
Alismataceae, such as
  Alisma spp.
  etc.
  Sagittaria sagittifolia The amount used of the agents according to the invention may vary and depends in essence on the type of effect to be achieved; it is generally from 0.1 to 15 (and more), preferably from 0.2 to 6, kg per hectare of active ingredient.

The herbicides according to the invention may be used in cereals such as

Avena spp.
  Triticum spp
  Hordeum spp.
  Secale spp.
  Saccharum officinarum
  Sorghum
  Zea mays
  Panicum miliaceum
  Oryza spp.

and in dicotyledon crops such as
Cruciferae, e.g.
  Brassica spp.
  Sinapis spp.
  Raphanus spp.
  Lepidium spp.
Compositae, e.g.
  Lactuca spp.
  Helianthus spp.
  Carthamus spp.
  Scorzonera spp.
Malvaceae, e.g.
  Gossypium hirsutum
Leguminosae, e.g.
  Medicago spp.
  Trifolium spp.
  Pisum spp.
  Phaseolus spp.
  Arachis spp.
  Glycine max.
Chenopodiaceae, e.g.
  Beta vulgaris
  Spinacia spp.
Solanaceae, e.g.
  Solanum spp.
  Nicotiania spp.
  Capsicum annuum
Linaceae, e.g.
  Linum spp.
Umbelliferae, e.g.
  Petroselinum spp.
  Daucus carota
  Apium graveolens
Rosaceae, e.g.
  Fragaria
Cucurbitaceae, e.g.
  Cucumis spp.
  Cucurbita spp.
Liliaceae, e.g.
  Allium spp.
Vitaceae, e.g.
  Vitis vinifera
Bromeliaceae, e.g.
  Ananas sativus.

Applications may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphtalene, alkylated naphthalenes and their derivatives such as methanol, ethanol, propanol, butanol, chloroform, carbon tetrachloride, cyclohexanol, cyclohexanone, chlorobenzene, isophorone, etc. and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalene-sulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonted naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol ethers, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90% by weight of active ingredient.

There may be added to the compositions or individual active ingredients (if desired, immediately before use (tank-mix)) oils of various types, herbicides, fungicides, nematocides, insecticides, bactericides, trace elements, fertilizers, antifoams (e.g., silicones), growth regulators, antidotes and other herbicidally effective compounds such as
substituted anilines
substituted aryloxycarboxylic acids and salts, esters and amides thereof,
substituted ethers
substituted arsonic acids and their salts, esters and amides
substituted benzimidazoles
substituted benzisothiazoles
substituted benzothiadiazinone dioxides
substituted benzoxazines
substituted benzoxadinones
substituted benzothiadiazoles
substituted biurets
substituted quinolines
substituted carbamates
substituted aliphatic carboxylic acids and their salts, esters and amides
substituted aromatic carboxylic acids and their salts, esters and amides
substituted carbamoylalkylthiol- or dithiophosphates
substituted quinazolines
substituted cycloalkylamidocarbothiolic acids and their salts, esters and amides
substituted cycloalkylcarbonamidothiazoles
substituted dicarboxylic acids and their salts, esters and amides
substituted dihydrobenzofuranyl sulfonates
substituted disulfides
substituted dipyridylium salts
substituted dithiocarbamates
substituted dithiophosphoric acids and their salts, esters and amides
substituted ureas
substituted hexahydro-1H-carbothioates
substituted hydantoins
substituted hydrazides
substituted hydrazonium salts
substituted isoxazole pyrimidones
substituted imidazoles
substituted isothiazole pyrimidones
substituted ketones
substituted naphthoquinones
substituted aliphatic nitriles
substituted aromatic nitriles
substituted oxadiazoles
substituted oxadiazinones
substituted oxadiazolidone diones
substituted oxadiazine diones
substituted phenols and their salts and esters
substituted phosphonic acids and their salts, esters and amides
substituted phosphonium chlorides
substituted phosphonalkyl glycines
substituted phosphites
substituted phosphoric acids and their salts, esters and amides
substituted piperidines
substituted pyrazoles substituted pyrazole alkylcarboxylic acids and their salts, esters and amides
substituted pyrazolium salts
substituted pyrazolium alkyl sulfates
substituted pyridazines
substituted pyridazones
substituted pyridine carboxylic acids and their salts, esters and amides
substituted pyridines
substituted pyridine carboxylates
substituted pyridinones
substituted pyrimidines
substituted pyrimidones
substituted pyrrolidone carboxylic acid and its salts, esters and amides
substituted pyrrolidines
substituted pyrrolidones
substituted arylsulfonic acids and their salts, esters and amides
substituted styrenes
substituted tetrahydrooxadiazine diones
substituted tetrahydroxadiazole diones
substituted tetrahydromethanoindenes
substituted tetrahydroxadiazole thiones
substituted tetrahydrothiadiazine thiones
substituted tetrahydrothiadiazole diones
substituted aromatic thiocarbonylamides
substituted thiocarboxylic acids and their salts, esters and amides
substituted thiol carbamates
substituted thioureas
substituted thiophosphoric acids and their salts, esters and amides
substituted triazines
substituted triazoles
substituted uracils, and
substituted uretidine diones.

The last-mentioned herbicidal compounds may also be applied before or after the active ingredients or compositions thereof according to the invention.

These agents may be added to the herbicides according to the invention in a ratio by weight of from 1:10 to 10:1. The same applies to oils, fungicides, nematocides, insecticides, bactericides, antidotes and growth regulators.

The herbicides according to the invention may be used one or more times before or after planting, before sowing, preemergence, postemergence or during emergence of the crop or unwanted plants.

EXAMPLE 9

In the greenhouse, loamy sandy soil was filled into pots and sown with the seeds of various plants. The soil was immediately treated with 2 kg per hectare of each of the following active ingredients, each being dispersed, emulsified or dissolved in 500 liters of water per hectare:

2,3-dihydro-3,3-dimethyl-2-ethoxybenzofuran-5-yl methylaminosulfate, sodium salt (I)

2,3-dihydro-3,3-dimethyl-2-ethoxybenzofuran-5-yl-N-methylcarbonyl methylaminosulfonate (II)

2,3-dihydro-3,3-dimethyl-2-ethoxybenzofuran-5-yl-N-chloromethylcarbonyl methylaminosulfonate (III)

2,3-dihydro-3,3-dimethyl-2-methoxybenzofuran-5-yl-N-methylcarbonyl methylaminosulfonate (IV)

2,3-dihydro-3,3-dimethyl-2-methoxybenzofuran-5-yl-N-chloromethylcarbonyl methylaminosulfonate (V)

2,3-dihydro-3,3-dimethyl-2-methylcarbonyloxybenzofuran-5-yl-N-methylcarbonyl methylaminosulfonate (VI)

2,3-dihydro-3,3-dimethyl-2-ethoxybenzofuran-5-yl-N-methoxycarbonyl methylaminosulfonate (VII)

2,3-dihydro-3,3-dimethyl-2-ethoxybenzofuran-5-yl-N-ethoxycarbonyl methylaminosulfonate (VIII)

2,3-dihydro-3,3-dimethyl-2-ethoxybenzofuran-5-yl-N-isopropoxycarbonyl methylaminosulfonate (IX)

2,3-dihydro-3,3-dimethyl-2-methoxycarbonyloxybenzofuran-5-yl dimethylaminosulfonate (X)

2,3-dihydro-3,3-dimethyl-2-ethoxycarbonyloxybenzofuran-5-yl dimethylaminosulfonate (XI)

2,3-dihydro-3,3-dimethyl-2-methoxycarbonyloxybenzofuran-5-yl diethylaminosulfonate (XII) and, for comparison, 2-ethoxy-2,3-dihydro-3,3-dimethyl-5-benzofuranyl methanesulfonate (XIII)

2,3-dihydro-3,3-dimethyl-2-isopropoxybenzofuran-5-yl ethylaminosulfonate (XIV).

After 4 to 5 weeks it was ascertained that active ingredients I to XII had a better herbicidal action than compounds XIII and XIV, combined with the same crop plant compatibility.

The results are given below:

| Active ingredient kg/ha | I 2 | II 2 | III 2 | IV 2 | V 2 | VI 2 | VII 2 |
|---|---|---|---|---|---|---|---|
| Crop plants: | | | | | | | |
| Beta spp. | 0 | 0 | 0 | 0 | 0 | 0 | 0 |
| Brassica napus | 10 | 5 | 0 | 0 | 0 | 0 | 0 |
| Phaseolus vulgaris | 0 | 0 | 0 | 0 | 0 | 0 | 0 |
| Helianthus annuus | 0 | 0 | 0 | 0 | 0 | 0 | 0 |
| Unwanted plants: | | | | | | | |
| Avena fatua | 100 | 100 | 98 | 95 | 95 | 90 | 95 |
| Alopecurus myosuroides | 100 | 100 | 100 | 100 | 100 | 90 | 100 |
| Echinochloa crus-galli | 100 | 95 | 95 | 96 | 95 | 90 | 95 |
| Lolium multiflorum | 100 | 100 | 100 | 100 | 100 | 80 | 100 |
| Poa annua | 100 | 100 | 97 | 100 | 100 | 90 | 100 |
| Sinapis arvensis | 80 | 65 | 55 | 50 | 50 | 40 | 60 |

| Active ingredient kg/ha | VIII 2 | IX 2 | X 2 | XI 2 | XII 2 | XIII 2 | XIV 2 |
|---|---|---|---|---|---|---|---|
| Crop plants: | | | | | | | |
| Beta spp. | 0 | 0 | 0 | 0 | 0 | 10 | 0 |
| Brassica napus | 0 | 0 | 0 | 0 | 0 | 5 | 10 |
| Phaseolus vulgaris | 0 | 0 | 0 | 0 | 0 | 5 | 0 |
| Helianthus annuus | 0 | 0 | 0 | 0 | 0 | 10 | 0 |
| Unwanted plants: | | | | | | | |
| Avena fatua | 95 | 90 | 100 | 95 | 95 | 80 | 90 |
| Alopecurus myosuroides | 95 | 90 | 100 | 100 | 95 | 85 | 80 |
| Echinochloa crus-galli | 95 | 95 | 100 | 95 | 90 | 80 | 30 |

-continued

| Active ingredient kg/ha | I 2 | II 2 | III 2 | IV 2 | V 2 | VI 2 | VII 2 |
|---|---|---|---|---|---|---|---|
| Lolium multiflorum | 95 | 95 | 100 | 95 | 90 | 80 | 50 |
| Poa annua | 98 | 95 | 100 | 100 | 95 | 85 | 65 |
| Sinapis arvensis | 45 | 40 | 75 | 60 | 55 | 20 | 30 |

0 = no damage
100 = complete destruction

EXAMPLE 10

In the greenhouse, various plants were treated at a growth height of from 2 to 15 cm with 2 kg per hectare of each of active ingredients I to XIV (as defined in Example 9), each being emulsified, dispersed or dissolved in 500 liters of water per hectare.

After 2 to 3 weeks it was ascertained that active ingredients I to XII had a better herbicidal action than compounds XIII and XIV, combined with the same crop plant compatibility.

The results are given below:

EXAMPLE 11

In the greenhouse, loamy sandy soil was filled into pots and sown with the seeds of various plants. The soil was then immediately treated with 3 kg per hectare of each of the following active ingredients, each being dispersed or emulsified in 500 liters of water per hectare:

2,3-dihydro-3,3-dimethyl-2-ethoxybenzofuran-5-yl-N-methylcarbonyl methylaminosulfonate (II)
2,3-dihydro-3,3-dimethyl-2-ethoxybenzofuran-5-yl-N-chloromethylcarbonyl methylaminosulfonate

| Active ingredient kg/ha | I 2 | II 2 | III 2 | IV 2 | V 2 | VI 2 | VII 2 |
|---|---|---|---|---|---|---|---|
| Crop plants: | | | | | | | |
| Beta spp. | 0 | 0 | 0 | 0 | 0 | 0 | 0 |
| Brassica napus | 0 | 0 | 0 | 0 | 0 | 0 | 0 |
| Unwanted plants: | | | | | | | |
| Avena fatua | 100 | 98 | 90 | 95 | 95 | 90 | 95 |
| Echinochloa crus-galli | 90 | 90 | 85 | 85 | 85 | 85 | 85 |
| Poa annua | 100 | 97 | 90 | 98 | 95 | 90 | 95 |
| Alopecurus myosuroides | 95 | 95 | 90 | 95 | 95 | 85 | 95 |

| Active ingredient kg/ha | VIII 2 | IX 2 | X 2 | XI 2 | XII 2 | XIII 2 | XIV 2 |
|---|---|---|---|---|---|---|---|
| Crop plants: | | | | | | | |
| Beta spp. | 0 | 0 | 0 | 0 | 0 | 20 | 0 |
| Brassica napus | 0 | 0 | 10 | 0 | 5 | 30 | 0 |
| Unwanted plants: | | | | | | | |
| Avena fatua | 96 | 90 | 95 | 90 | 85 | 75 | 90 |
| Echinochloa crus-galli | 86 | 85 | 100 | 95 | 90 | 70 | 85 |
| Poa annua | 97 | 90 | 100 | 95 | 90 | 70 | 85 |
| Alopecurus myosuroides | 97 | 85 | 100 | 100 | 95 | 90 | 80 |

0 = no damage
100 = complete destruction

The action of the following compounds corresponds to that of the compounds according to the invention in the foregoing examples:

2,3-dihydro-3,3-dimethyl-2-methoxybenzofuran-5-yl-N-methylsulfonyl methylaminosulfonate
2,3-dihydro-3,3-dimethyl-2-methoxycarbonyloxybenzofuran-5-yl diethylaminosulfonate
2,3-dihydro-3,3-dimethyl-2-methoxycarbonyloxybenzofuran-5-yl dimethylaminosulfonate
2,3-dihydro-3,3-dimethyl-2-ethoxycarbonylbenzofuran-5-yl dimethylaminosulfonate (III)
2,3-dihydro-3,3-dimethyl-2-ethoxybenzofuran-5-yl-N-methoxycarbonyl methylaminosulfonate (VII)
2,3-dihydro-3,3-dimethyl-2-ethoxybenzofuran-5-yl-N-ethoxycarbonyl methylaminosulfonate (VIII)
and, for comparison,
2-ethoxy-2,3-dihydro-3,3-dimethyl-5-benzofuranyl methanesulfonate (XIII).

During the experiment the plants were watered well.

After 3 to 4 weeks it was ascertained that active ingredients II, III, VII and VIII had better crop plant compatibility than compound XIII, combined with the same herbicidal action.

The results are given below:

| Active ingredient kg/ha | II 3 | III 3 | VII 3 | VIII 3 | XIII 3 |
|---|---|---|---|---|---|
| Crop plants: | | | | | |
| Gossypium hirsutum | 5 | 0 | 5 | 10 | 40 |
| Zea mays | 20 | 5 | 10 | 15 | 60 |
| Beta spp. | 10 | 0 | 5 | 5 | 30 |
| Unwanted plants: | | | | | |
| Echinochloa crus-galli | 100 | 100 | 100 | 100 | 100 |
| Setaria faberii | 100 | 100 | 100 | 100 | 100 |
| Alopecurus myosuroides | 100 | 100 | 100 | 100 | 100 |
| Avena fatua | 100 | 100 | 100 | 100 | 100 |

| Active ingredient kg/ha | II 3 | III 3 | VII 3 | -continued VIII 3 | XIII 3 |
|---|---|---|---|---|---|
| Galium aparine | 100 | 100 | 100 | 100 | 100 |

0 = no damage
100 = complete destruction

We claim:
1. A compound of the formula

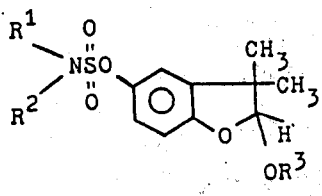

wherein:
R¹ denotes hydrogen, unsubstituted or chloro- or methoxy-substituted alkyl of 1–4 carbon atoms, allyl, methallyl, propargyl or butynyl;
2. 2,3-dihydro-3,3-dimethyl-2-ethoxybenzofuran-5-yl methylaminosulfonate, sodium salt.
3. 2,3-dihydro-3,3-dimethyl-2-ethoxybenzofuran-5-yl methylaminosulfonate, potassium salt.
4. 2,3-dihydro-3,3-dimethyl-2-ethoxybenzofuran-5-yl-N-methylcarbonyl methylaminosulfonate.
5. 2,3-dihydro-3,3-dimethyl-2-ethoxybenzofuran-5-yl-N-chloromethylcarbonyl methylaminosulfonate.
6. 2,3-dihydro-3,3-dimethyl-2-methoxybenzofuran-5-yl-N-methylcarbonyl methylaminosulfonate.
7. 2,3-dihydro-3,3-dimethyl-2-methoxybenzofuran-5-yl-N-chloromethylcarbonyl methylaminosulfonate.
8. 2,3-dihydro-3,3-dimethyl-2-methylcarbonyloxybenzofuran-5-yl-N-methylcarbonyl methylaminosulfonate.
9. 2,3-dihydro-3,3-dimethyl-2-ethoxybenzofuran-5-yl-N-methoxycarbonyl methylaminosulfonate.
10. 2,3-dihydro-3,3-dimethyl-2-ethoxybenzofuran-5-yl-N-ethoxycarbonyl methylaminosulfonate.
11. 2,3-dihydro-3,3-dimethyl-2-ethoxybenzofuran-5-yl-N-isopropoxycarbonyl methylaminosulfonate.
12. 2,3-dihydro-3,3-dimethyl-2-methoxybenzofuran-5-yl-N-methylsulfonyl methylaminosulfonate.

* * * * *